United States Patent
Zahiri

(12) 
(10) Patent No.: US 7,112,182 B1
(45) Date of Patent: Sep. 26, 2006

(54) DYNAMIC ANKLE PROTECTION APPARATUS

(76) Inventor: Hormoz Zahiri, 11718 Chenault St., Los Angeles, CA (US) 90049

( * ) Notice: Subject to any disclaimer, the term of this patent is extended or adjusted under 35 U.S.C. 154(b) by 0 days.

(21) Appl. No.: 11/189,156

(22) Filed: Jul. 25, 2005

(51) Int. Cl.
    *A61F 5/00* (2006.01)
(52) U.S. Cl. ............... 602/27; 602/23; 602/28; 602/29; 128/882
(58) Field of Classification Search ............ 602/5, 602/23, 27, 28, 29; 128/869, 882
    See application file for complete search history.

(56) References Cited

U.S. PATENT DOCUMENTS

| | | | |
|---|---|---|---|
| 2,656,834 A * | 10/1953 | Hatkoff | 602/27 |
| 4,523,394 A * | 6/1985 | Lindh et al. | 36/89 |
| 4,556,054 A * | 12/1985 | Paulseth | 602/27 |
| 4,646,726 A * | 3/1987 | Westin et al. | 602/27 |
| 4,753,229 A * | 6/1988 | Sutherland | 602/27 |
| 4,982,733 A * | 1/1991 | Broadhurst et al. | 602/27 |
| 4,992,630 A * | 2/1991 | Mletzko | 178/19.04 |
| 5,217,431 A * | 6/1993 | Toronto et al. | 602/27 |
| 5,672,156 A * | 9/1997 | Jimenez Ramos | 602/27 |
| 5,792,087 A * | 8/1998 | Pringle | 602/27 |
| 6,447,469 B1* | 9/2002 | Ritchie | 602/27 |
| 6,503,218 B1* | 1/2003 | Ascheman | 602/23 |

\* cited by examiner

*Primary Examiner*—Henry Bennett
*Assistant Examiner*—Amanda Wieker
(74) *Attorney, Agent, or Firm*—Thomas I. Rozsa

(57) ABSTRACT

An ankle support apparatus which is designed to protect the lateral maleolus ankle bone and the medial maleolus ankle bone. A cuff band is wrapped around the leg and a pair of elongated strap members are supported on the cuff band and on the shoe worn on the leg so that one elongated strap member is in front of the ankle bone and the other elongated strap member is behind the ankle bone.

10 Claims, 1 Drawing Sheet

DYNAMIC ANKLE PROTECTION APPARATUS

BACKGROUND OF THE INVENTION

1. Field of the Invention

The present invention relates to the field of athletic support devices and sports medicine. The devices are used to assist in the support of and protection of body parts.

2. Description of the Prior Art

In general, devices that are used to provide support to the ankles are known in the prior art. To the best of the inventor's knowledge, the prior art devices consist of constricting wraps or splints that go around the foot and lower leg at the location of the ankle. While such devices provide support to the ankle and enable the wearer to walk or run in an improved manner, such devices do not provide a specific support and protection of the injured ankle ligaments during an athletic event. There is a significant need for an improved device to provide support to the ankle during sports activities with specificity towards the protection of the anatomically known ligaments of the ankle joint and with elimination of the restricting effect on the other injured anatomical structures of the ankle joint. In other words, the uninjured tissues or the tissues not proven to be the usual athletic injury should not be unnecessarily restricted. The restricting mechanism should only partially limit the stretchability of the injured ligaments of the ankle joint and avoid a new or further injury to these ligaments.

SUMMARY OF THE INVENTION

The present invention is an ankle support apparatus which is designed to protect the lateral ankle ligaments or the medial ankle ligaments. A soft well-folded wide cuff band is wrapped around the lower leg along the ankle and a pair of elongated strap members are connecting the cuff band and the side of the shoe worn on the leg so that one elongated strap member is in front of the ankle lateral or medial maleolus and the other elongated strap member is behind the ankle medial or lateral maleolus.

It has been discovered, according to the present invention, that if means are provided to support the leg at the location of the ankle with the means put in front of and behind either ankle bone maleoli to mimic the ligaments of the ankle joint, then these ligaments will be shielded from being over strained and will be protected during vigorous sports activity.

It is therefore an object of the present invention to provide a means positioned both in front of and in back of either ankle bone maleoli to protect the related ligaments during vigorous athletic activity.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
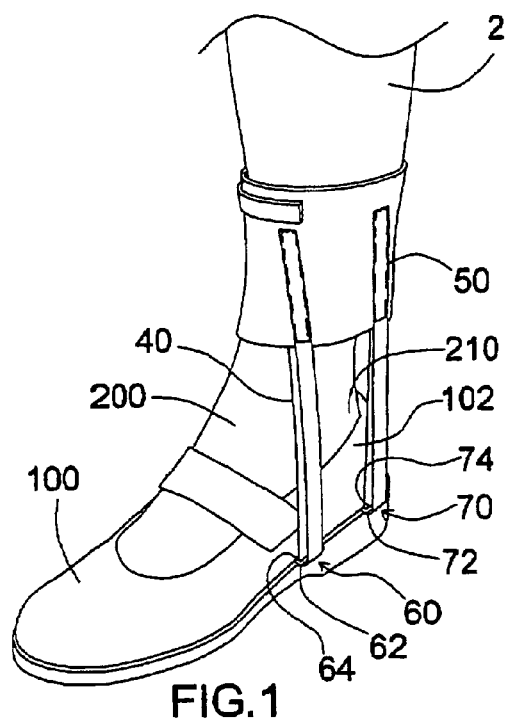
FIG. 1 is a perspective view of the present invention ankle protection apparatus worn outside of a leg to protect the outside ankle ligaments attached to the lateral maleolus.
Figure 2:
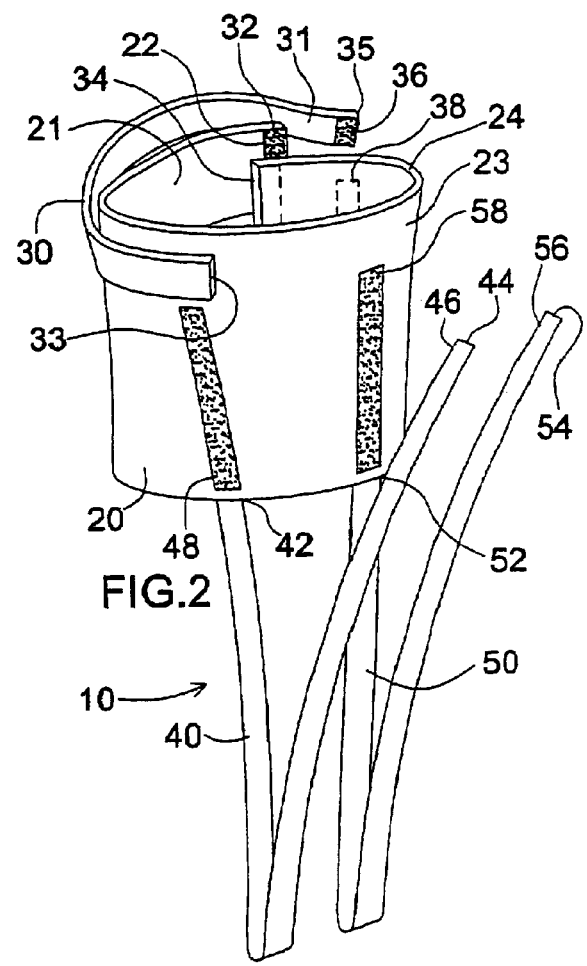
FIG. 2 is a perspective view of the present invention ankle protection apparatus in the opened condition to illustrate its closure means.
Figure 3:
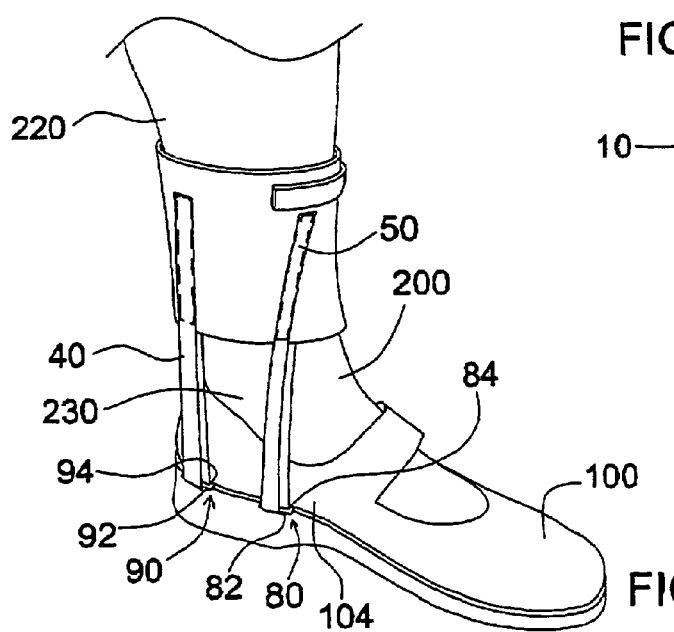
FIG. 3 is a perspective view of the present invention ankle protection apparatus worn on the inside of a leg to protect the inside ankle ligaments attached to the medial maleolus.

Referring to FIG. 2, there is illustrated the present invention ankle protection apparatus 10. The ankle protection apparatus comprises a cuff band 20 which is openable at location 22 so that the cuff band 20 can be wrapped around a lower leg immediately along the ankle, as illustrated in FIGS. 1 and 3. The cuff band 20 has a body 24 and an attached strap member 30. The body 24 and attached strap member 30 each have mating closure means which are attachable to mating closure means on the body 24 so that the cuff band 20 can be snugly wrapped around the lower leg. The closure members illustrated in FIG. 2 are mating hook and loop closure members known as Velcro®. It will be appreciated that other mating closure members such as snaps and other available means are also within the spirit and scope of the present invention. As illustrated in FIG. 2, the interior surface 21 of body 20 has a closure member 32 adjacent its open end which mates with a first closure member 34 on the exterior surface 23 of body 20 and the strap member 30 has a mating closure member 36 on its interior surface 31 adjacent its open end 35 which mates with a second closure member 38 on the exterior surface 23 of body 20. It will be appreciated that strap member 30 is permanently attached to the exterior surface 23 of body 20 at the opposite end 33 of strap member 30.

The additional components of the ankle support apparatus 10 are a pair of elongated strap members. First elongated strap member 40 is permanently attached at one end 42 to the interior surface 21 of cuff band 20 and at its opposite open end 44 has a mating closure member 46 which mates with a first closure member 48 on the exterior surface 23 of cuff band 20. Similarly, second elongated strap member 50 is permanently attached at one end 52 to the interior surface 21 of cuff band 20 and at its opposite open end 54 has a mating closure member 56 which mates with a second closure member 58 on the exterior surface 23 of cuff band 20. It will be appreciated that closure members 46, 48, 56 and 58 can be hook and loop fasteners known as Velcro®, mating snap fasteners, or any other type of closure members.

The ankle support apparatus 10 is worn so that the elongated bands are either adjacent the outside of a leg or adjacent the inside of a leg. In order to operate, the shoe with which the ankle support apparatus is used must have a pair of receiving and connecting members to accommodate an elongated bands.

Referring to FIG. 1, the ankle support apparatus 10 is illustrated with the elongated strap members adjacent the outside of the leg. Shoe 100 has a first receiving and connecting member 60 which is an elongated ring 62 with an opening 64. The receiving and connecting member 60 is permanently attached to an exterior surface 102 of shoe 100 so that the first receiving and connecting member 60 protrudes outwardly from the exterior surface 102 of shoe 100 as illustrated in FIG. 1. Shoe 100 also has a second receiving and connecting member 70 which is an elongated ring 72 with an opening 74. The receiving and connecting member 70 is permanently attached to an exterior surface 102 of shoe 100 so that the second receiving and connecting member 70 protrudes outwardly from the exterior surface 102 of shoe 100 as illustrated in FIG. 1. The two receiving and connecting members are at the same vertical location on the shoe 100 and spaced apart from one another.

The leg 200 has an exterior ankle bone known as the lateral malleolus 210. A key feature of the present invention is that the first elongated strap member 40 must be in front of the lateral malleolus 210 while the second elongated strap member 50 must be in back of the lateral malleolus 210. The strap members 40 and 50 can be of any shape and any material. The cross section can be round, rectangular, square, etc. As illustrated in FIG. 1, the cuff band 20 is unwrapped around leg 200 at a location just below calf 220 so that closure members 32 and 34 cause the body 24 to be wrapped around the leg 200 and closure members 36 and 38 of strap member 30 enable the body 24 of cuff band 20 to be tightly wrapped around leg 200. First elongated strap member 40 extends through opening 64 in receiving and connecting member 60 and then mating members 46 and 48 are connected so that first elongated strap member 40 is tight. Similarly, second elongated strap member 50 extends through opening 74 in receiving and connecting member 70 and then mating members 56 and 58 are connected so that second elongated strap member 50 is tight. Through use of the present invention ankle support apparatus 10, the elongated strap members 40 and 50 which are tightly maintained on the leg and shoe and are on either side of the lateral malleolus 210 prevent the ankle bone 210 from extending far outwardly during vigorous sports activities and thereby protect the ankle.

Referring to FIG. 3, the ankle support apparatus 10 is illustrated with the elongated strap members adjacent the inside of the leg 200. Shoe 100 has a third receiving and connecting member 90 which is an elongated ring 92 with an opening 94. The receiving and connecting member 90 is permanently attached to an outside interior surface 104 of shoe 100 so that the third receiving and connecting member 90 protrudes outwardly from the exterior surface 104 of shoe 100 as illustrated in FIG. 3. Shoe 100 also has a fourth receiving and connecting member 80 which is an elongated ring 82 with an opening 84. The receiving and connecting member 80 is permanently attached to an outside interior surface 104 of shoe 100 so that fourth receiving and connecting member 80 protrudes outwardly from the interior surface 104 of shoe 100 as illustrated in FIG. 3. The two receiving and connecting members are at the same vertical location on the shoe 100 and spaced apart from one another.

The receiving and connecting members 60, 70, 80 and 90 can each have an interior screw member such that they can be attached into any type of athletic shoe or any other wearing apparel.

The leg 200 has an interior ankle bone known as the medial malleolus 230. A key feature of the present invention is that the first elongated strap member 40 must be in back of the medial malleolus 230 while the second elongated strap member 50 must be in front of the medial malleolus 220. As illustrated in FIG. 3, the cuff band 20 is wrapped around leg 200 at a location just below calf 220 so that closure members 32 and 34 cause the body 24 to be wrapped around the leg 200 and closure members 36 and 38 of strap member 30 enable the body 24 of cuff band 20 to be tightly wrapped around leg 200. First elongated strap member extends through opening 94 in receiving and connecting member 90 and then mating members 46 and 48 are connected so that first elongated strap member 40 is tight. Similarly, second elongated strap member 50 extends through opening 84 in receiving and connecting member 80 and then mating members 56 and 58 are connected so that second elongated strap member 50 is tight. Through use of the present invention, ankle support apparatus 10, the elongated strap members 40 and 50 which are tightly maintained on the leg and shoe and are on either side of the medial malleolus 230 prevent the ankle bone 230 from extending too far inwardly during vigorous sports activities and thereby protect the ankle.

The components of the ankle support apparatus 10 can be made of any suitable material such as neoprene.

While the cuff band 20 is preferably below the calf, it can also be located at any location on the leg where the ankle is to be protected.

Defined in detail, the present invention is an ankle support apparatus to be used in conjunction with a leg having a calf and a shoe having an exterior surface, the ankle support apparatus to be used to protect the lateral malleolus of the leg, comprising: (a) an openable cuff band having a body with mating closure members on an interior surface and exterior surface of the body, and a strap member permanently attached at one end to the exterior surface of the body and having mating closure members on the interior surface of the strap member adjacent its opposite end and on the exterior surface of the body; (b) a first elongated strap member permanently attached at one end to the body of the cuff band and having a mating closure member at its opposite end which mates with a closure member on the body of the cuff band; (c) a second elongated strap member permanently attached at one end to the body of the cuff band and having a mating closure member at its opposite end which mates with a closure member on the body of the cuff band, the first and second elongated strap members being spaced apart; (d) a first receiving and connecting member attached to the exterior surface of the shoe, and having an elongated ring with an opening, the first receiving and connecting member extending outwardly from the shoe; (e) a second receiving and connecting member attached to the exterior surface of the shoe, and having an elongated ring with an opening, the second receiving and connecting member extending outwardly from the shoe, the first and second receiving and connecting members spaced apart and being at the same vertical height location on the exterior surface of the shoe; and (f) the cuff band wrapped around the leg so that the closure members on the cuff band and the strap enable the cuff band to be tightly wrapped around the leg at a location below the calf, the first elongated strap member extending through the opening in the first receiving and connecting member and thereafter connected to the cuff band so that it is tight, the second elongated strap member extending through the opening in the second receiving and connecting member and thereafter connected to the cuff band so that it is tight, the first elongated strap member located in front of the lateral malleolus and the second elongated strap member located in back of the lateral malleolus.

Defined alternatively, the present invention is an ankle support apparatus to be used in conjunction with a leg having a calf and a shoe having an outside interior surface, the ankle support apparatus to be used to protect the medial malleolus of the leg, comprising: (a) an openable cuff band having a body with mating closure members on an interior surface and exterior surface of the body, and a strap member permanently attached at one end to the exterior surface of the body and having mating closure members on the interior surface of the strap member adjacent its opposite end and on the exterior surface of the body; (b) a first elongated strap member permanently attached at one end to the body of the cuff band and having a mating closure member at its opposite end which mates with a closure member on the body of the cuff band; (c) a second elongated strap member permanently attached at one end to the body of the cuff band and having a mating closure member at its opposite end which mates with a closure member on the body of the cuff band, the first and second elongated strap member being spaced apart; (d) a first receiving and connecting member attached to the outside interior surface of the shoe, and having an elongated ring with an opening, the first receiving and connecting member extending outwardly from the outside interior surface of the shoe; (e) a second receiving and connecting member attached to the outside interior surface of the shoe, and having an elongated ring with an opening, the second receiving and connecting member extending outwardly from the outside interior surface of the shoe, the first and second receiving and connecting members spaced apart and being at the same vertical height location on the outside interior surface of the shoe; and (f) the cuff band wrapped around the leg so that the closure members on the cuff band and the strap enable the cuff band to be tightly wrapped around the leg at a location below the calf, the first elongated strap member extending through the opening in the first receiving and connecting member and thereafter connected to the cuff band so that it is tight, the second elongated strap member extending through the opening in the second receiving and connecting member and thereafter connected to the cuff band so that it is tight, the first elongated strap member located in back of the medial maleolus and the second elongated strap member located in front of the medial maleolus.

Defined broadly, the present invention is an ankle support apparatus to be used in conjunction with a leg and a shoe, the ankle support apparatus to be used to protect an ankle bone, comprising: (a) an openable cuff band having closure means to enable the cuff band to be tightly wrapped around a leg at a location above the ankle; (b) a first elongated strap member permanently attached at one end to the cuff band and having closure means at its opposite end so that the opposite end can be removably attached to the cuff band; (c) a second elongated strap member permanently attached at one end to the cuff band and having closure means at its opposite end so that the opposite end can be removably attached to the cuff band; (d) a first receiving means attached to an exterior surface of the shoe and a spaced apart second receiving means attached to the same exterior surface of the shoe; and (e) the cuff band wrapped around the leg and the first elongated strap member extending through the first receiving means and connected to the cuff band so that the first elongated strap member is tight and the second elongated strap member extending through the second receiving means and connected to the cuff band so that the second elongated strap member is tight, the first elongated strap member located on one side of the ankle and the second elongated strap member located on the opposite side of the ankle.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. An ankle support apparatus to be used in conjunction with a leg having a calf and a shoe having an exterior surface, the ankle support apparatus to be used to protect the lateral maleolus of the leg, comprising:
    a. an openable cuff band having a body with mating closure members on an interior surface and exterior surface of the body, and a strap member permanently attached at one end to the exterior surface of the body and having mating closure members on the interior surface of the strap member adjacent its opposite end and on the exterior surface of the body;
    b. a first elongated strap member permanently attached at one end to the body of the cuff band and having a mating closure member at its opposite end which mates with a closure member on the body of the cuff band;
    c. a second elongated strap member permanently attached at one end to the body of the cuff band and having a mating closure member at its opposite end which mates with a closure member on the body of the cuff band, the first and second elongated strap members being spaced apart;
    d. a first receiving and connecting member attached to the exterior surface of the shoe, and having an elongated ring with an opening, the first receiving and connecting member extending outwardly from the shoe;
    e. a second receiving and connecting member attached to the exterior surface of the shoe, and having an elongated ring with an opening, the second receiving and connecting member extending outwardly from the shoe, the first and second receiving and connecting members spaced apart and being at the same vertical height location on the exterior surface of the shoe; and
    f. the cuff band adapted to be wrapped around the leg so that the closure members on the cuff band and the strap enable the cuff band to be tightly wrapped around the leg at a location below the calf, the first elongated strap member extending through the opening in the first receiving and connecting member and thereafter connected to the cuff band so that it is tight, the second elongated strap member extending through the opening in the second receiving and connecting member and thereafter connected to the cuff band so that it is tight, the first elongated strap member being generally parallel to the second elongated strap member, the first elongated strap member located in front of the lateral maleolus and the second elongated strap member located in back of the lateral maleolus so that this positioning supports the lateral maleolus.

2. The ankle support apparatus in accordance with claim 1, wherein the cuff band, the first elongated strap member and the second elongated strap are made of neoprene.

3. The ankle support apparatus in accordance with claim 1, wherein all of the closure members are mating hook and loop fasteners.

4. An ankle support apparatus to be used in conjunction with a leg having a calf and a shoe having an outside interior surface, the ankle support apparatus to be used to protect the medial maleolus of the leg, comprising:
   a. an openable cuff band having a body with mating closure members on an interior surface and exterior surface of the body, and a strap member permanently attached at one end to the exterior surface of the body and having mating closure members on the interior surface of the strap member adjacent its opposite end and on the exterior surface of the body;
   b. a first elongated strap member permanently attached at one end to the body of the cuff band and having a mating closure member at its opposite end which mates with a closure member on the body of the cuff band;
   c. a second elongated strap member permanently attached at one end to the body of the cuff band and having a mating closure member at its opposite end which mates with a closure member on the body of the cuff band, the first and second elongated strap member being spaced apart;
   d. a first receiving and connecting member attached to the outside interior surface of the shoe, and having an elongated ring with an opening, the first receiving and connecting member extending outwardly from the outside interior surface of the shoe;
   e. a second receiving and connecting member attached to the outside interior surface of the shoe, and having an elongated ring with an opening, the second receiving and connecting member extending outwardly from the outside interior surface of the shoe, the first and second receiving and connecting members spaced apart and being at the same vertical height location on the outside interior surface of the shoe; and
   f. the cuff band adapted to be wrapped around the leg so that the closure members on the cuff band and the strap enable the cuff band to be tightly wrapped around the leg at a location below the calf, the first elongated strap member extending through the opening in the first receiving and connecting member and thereafter connected to the cuff band so that it is tight, the second elongated strap member extending through the opening in the second receiving and connecting member and thereafter connected to the cuff band so that it is tight, the first elongated strap member being generally parallel to the second elongated strap member, the first elongated strap member located in back of the medial maleolus and the second elongated strap member located in front of the medial maleolus so that this positioning supports the medial maleolus.

5. The ankle support apparatus in accordance with claim 4, wherein the cuff band, the first elongated strap member and the second elongated strap are made of neoprene.

6. The ankle support apparatus in accordance with claim 4, wherein all of the closure members are mating hook and loop fasteners.

7. An ankle support apparatus to be used in conjunction with a leg and a shoe, the ankle support apparatus to be used to protect an ankle bone, comprising:
   a. an openable cuff band having closure means to enable the cuff band to be tightly wrapped around a leg at a location above the ankle;
   b. a first elongated strap member permanently attached at one end to the cuff band and having closure means at its opposite end so that the opposite end can be removably attached to the cuff band;
   c. a second elongated strap member permanently attached at one end to the cuff band and having closure means at its opposite end so that the opposite end can be removably attached to the cuff band;
   d. a first receiving means attached to an exterior surface of the shoe and a spaced apart second receiving means attached to the same exterior surface of the shoe; and
   e. the cuff band adapted to be wrapped around the leg and said first elongated strap member extending through the first receiving means and connected to the cuff band so that the first elongated strap member is tight and the second elongated strap member extending through the second receiving means and connected to the cuff band so that the second elongated strap member is tight, the first elongated strap member being generally parallel to the second elongated strap member, the first elongated strap member located on one side of the ankle and the second elongated strap member located on the opposite side of the ankle so that this positioning supports the ankle.

8. The ankle support apparatus in accordance with claim 7, wherein the ankle to be protected is the lateral maleolus, further comprising:
   a. said first receiving means and said second receiving means are located on the outside outer surface of the shoe; and
   b. said first elongated strap member is located in front of the lateral maleolus and said second elongated strap member is located in back of the lateral maleolus.

9. The ankle support apparatus in accordance with claim 7, wherein the ankle to be protected is the medial maleolus, further comprising:
   a. said first receiving means and said second receiving means are located on the outside interior surface of the shoe; and
   b. said first elongated strap member is located in back of the medial maleolus and said second elongated strap member is located in front of the medial maleolus.

10. The ankle support apparatus in accordance with claim 7, wherein said cuff band is made of neoprene.

* * * * *